United States Patent [19]
Davies

[11] Patent Number: 5,285,162
[45] Date of Patent: Feb. 8, 1994

[54] GALVANIC CURRENT MEASURING METHOD AND APPARATUS FOR MONITORING BUILD-UP OF BIOLOGICAL DEPOSITS ON SURFACES OF DISSIMILAR METAL ELECTRODES IMMERSED IN WATER

[75] Inventor: James O. Davies, Gravesend, United Kingdom

[73] Assignee: National Power Plc, Swindon, England

[21] Appl. No.: 720,525

[22] PCT Filed: Dec. 20, 1989

[86] PCT No.: PCT/GB89/01522
   § 371 Date: Jun. 24, 1991
   § 102(e) Date: Jun. 24, 1991

[87] PCT Pub. No.: WO90/07710
   PCT Pub. Date: Jul. 12, 1990

[30] Foreign Application Priority Data
   Dec. 23, 1988 [GB] United Kingdom ......... 8830161

[51] Int. Cl.⁵ .................. G01N 27/42; C12M 1/34
[52] U.S. Cl. .......................... 324/425; 324/71.1; 73/61.62; 204/434; 435/291
[58] Field of Search ............ 324/71.1, 444, 699, 324/700, 425, 439, 446, 450, 713; 73/61.62, 61.63; 210/746; 204/434; 435/291

[56] References Cited

U.S. PATENT DOCUMENTS 4,576,704 3/1986 Chiusole et al. .
4,581,121 4/1986 Dailey et al. .
4,801,546 1/1989 Ackland .................. 324/71.1 X

OTHER PUBLICATIONS

Bridger Scientific, Inc., Deposit Accumulation Testing Systerm (DATS), Management Tools For Costly Fouling Problems... (Description and Price List), Aug. 13, 1987.
InTech Sep. 1985, Monitoring of Fouling Deposits: A Key to Heat Exchanger Management, by Frank L. Roe, Nick Zelver (BSI) and William G. Characklis, Montana State University, pp. 91-94.

Primary Examiner—Gerard R. Strecker
Assistant Examiner—Diep Do
Attorney, Agent, or Firm—Antonelli, Terry, Stout & Kraus

[57] ABSTRACT

The build-up of the deposits on surfaces immersed in water in monitored by passing the water through a galvanic cell comprising a pair of dissimilar metal electrodes (5, 6) mounted on opposite sides of a passage (4) for the water in a housing (1,7), and detecting and interpreting galvanic current developed between the electrodes (5, 6).

11 Claims, 2 Drawing Sheets

GALVANIC CURRENT MEASURING METHOD AND APPARATUS FOR MONITORING BUILD-UP OF BIOLOGICAL DEPOSITS ON SURFACES OF DISSIMILAR METAL ELECTRODES IMMERSED IN WATER

This invention relates to a monitoring method and apparatus, and in particular to a method of monitoring the build-up of deposits on surfaces immersed in water and to apparatus for carrying out such method.

Continuous chlorination of seawater cooling supplies for power stations during the summer months is advised to prevent the settlement and growth of species such as mussels which can induce corrosion of copper based condenser tubes and restriction of cooling water flow. Since titanium came into general use, the incentive to provide continuous chlorination for this purpose has diminished. However, chlorination or some other form of biocidal treatment is still required to control the growth of bacterial slime films which form the basis of a micro-fouling layer containing larger organisms, silt, etc. Preventing the formation of the slime film improves heat transfer and reduces the resistance to flow.

There is growing legislative pressure in the United States of America and the EEC to reduce or eliminate the discharge of active chlorine from power stations. This fact, together with a desire for economy in the use of chlorine (or sodium hypochlorite) and the lack of detailed knowledge on the change in the rate of biofouling throughout the year, indicate the need for techniques to monitor the build-up of biofouling films and the effect of anti-fouling procedures on them.

At present the existence of such films can be established only by inspection at outages or inferred indirectly from their effect on condenser performance (vacuum) changes, which may be due to other causes such as steamside fouling of the condenser tubes or maldistribution of steam flows and off-gases.

According to this invention there is provided a method of monitoring the build-up of deposits on surfaces immersed in water, characterised by the steps of passing water through a galvanic cell comprising a pair of dissimilar metal electrodes having means responsive to galvanic current developed between the electrodes connected across the elect-odes, and interpreting changes in the galvanic current developed to obtain an indication of the build-up of deposits on the electrodes.

The method of the invention derives from the fact that in water the degree of galvanic corrosion between metal couples incorporating-noble materials such as titanium and stainless steel depends- very largely on the reduction of oxygen on the cathodic surface. This process is controlled by the biochemical activity of bacterial species present on the cathode surface, and until a basic slime film forms very little current flows.

A rapid increase in galvanic current indicates full development of a slime film which is the precursor of subsequent growth of thicker fouling films.

This invention will now be described by way of example with reference to the drawing, in which.

Figure 1:
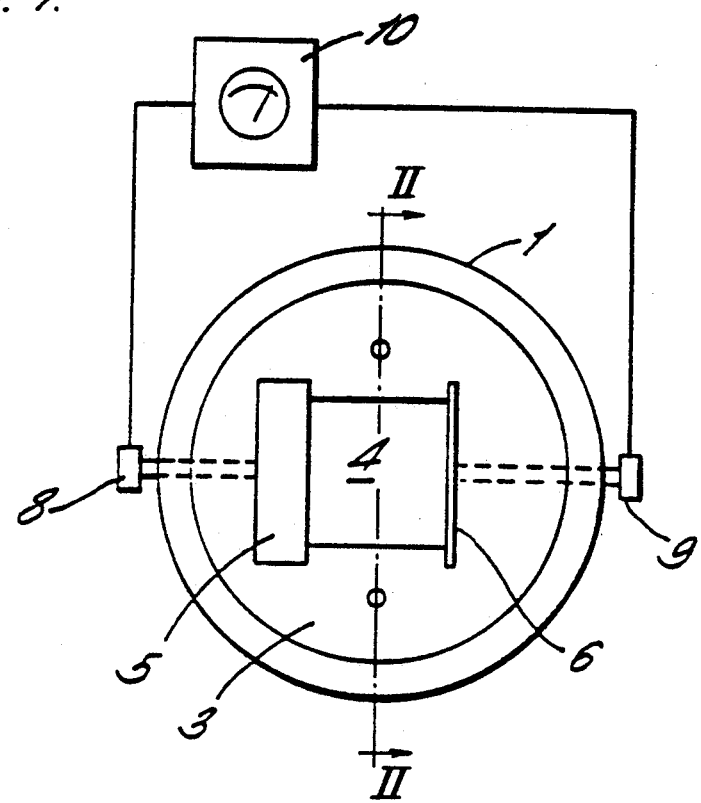
FIG. 1 is a sectional view of apparatus for use in carrying out the method of the invention and is taken along ling I—I in FIG. 2.
Figure 2:
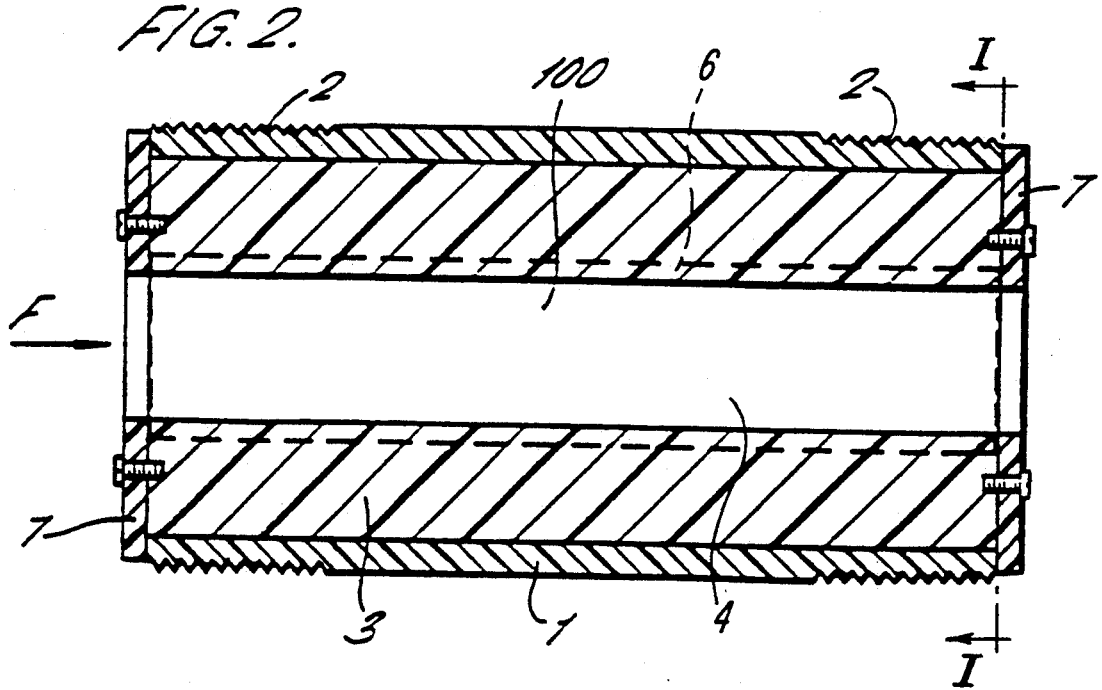
FIG. 2 is a longitudinal sectional view through the apparatus of FIG. 1 and is taken along line II—II in FIG. 1.

Referring to the drawings, the apparatus comprises a housing 1 formed by a PVC material tubular member having externally threaded end portions 2 by which the housing 1 can be connected to the cooling water system of a power station, through which seawater 100 flows. Located in the housing 1 is an insert member 3 of blocked PVC material, which defines a passage 4 for the seawater 100 flowing through the apparatus as indicated by arrow F in FIG. 2.

Mounted along opposite sides of the passage 4 and extending the length thereof are two dissimilar metal plate electrodes 5 and 6 having substantially equal area facing surfaces. The electrode 5 is of naval brass while the electrode 6 is of titanium. Otherwise electrodes of steel and stainless steel can be used.

The insert 3 and electrodes 5 and 6 are retained in the housing 1 by end plates 7 of PVC material.

Each of the electrodes 5 and 6 has connected thereto a contact member 8 or 9 which extends out of the housing 1, and a means 10 responsive to galvanic current developed between the electrodes 5 and 6 in use of the apparatus, for example a zero-resistance ammeter, is connected across the contacts 8 and 9.

In use, the apparatus is connected to the cooling seawater system of a power station, and the seawater flows through the passage 4 in the housing 1 between the electrodes 5 and 6. The apparatus functions as a galvanic cell, with the ammeter 10 indicating the galvanic current developed between the electrodes 5 and 6. As mentioned above, the value of the galvanic current developed is dependent upon the build-up of deposits, that is the slime film, on the surfaces of the electrodes 5 and 6, and changes in the current will be indicated by the ammeter 10. Thus, such changes in the galvanic current can be interpreted to obtain an indication of the extent of deposit build-up whereby it can be decided when action is necessary to remove such deposits from the cooling water tube in which the apparatus is mounted.

Figure 3:
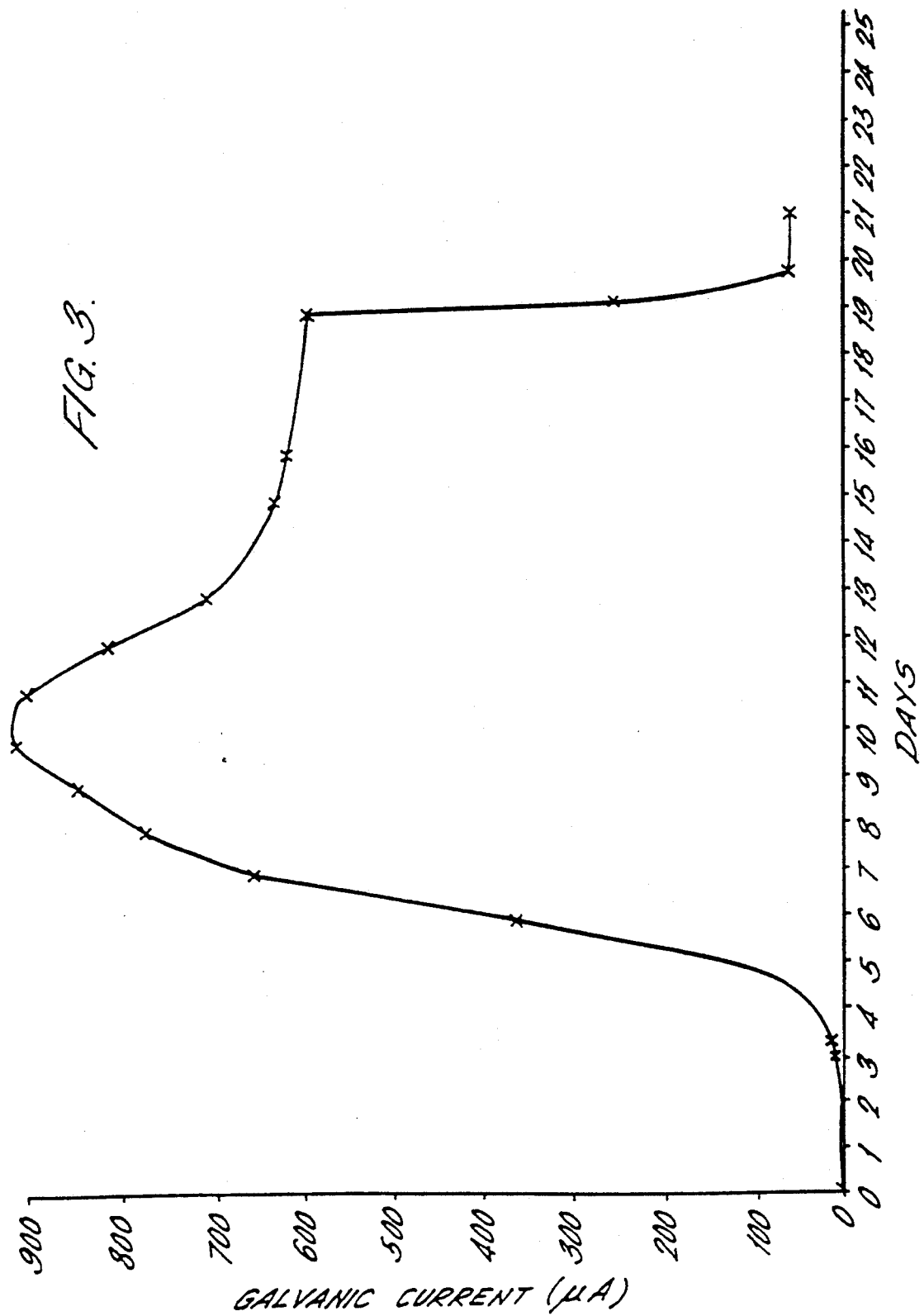
FIG. 3 is a graph illustrating operation of the apparatus of FIGS. 1 and 2.

FIG. 3 is a graph illustrating operation of an apparatus as described above, with galvanic current developed ($\mu A$) being plotted against time (in days) As shown, initially there is little galvanic current developed, but after two days the current begins to rise to reach a maximum in about ten days, and then falls off to a still relatively high level over the next nine days. On day nineteen action is taken to remove the deposits (the addition of chlorine to the seawater), and as clearly shown this has a rapid effect to reduce the galvanic current to a relatively low level, indicating that the deposits have been substantially removed from the electrodes 5 and 6.

The method and apparatus as described above have the advantages that they can provide a continuous record of fouling conditions in condenser tubes, heat exchangers and cooling water tubes of power stations, and enable controlled action to be taken to remove deposits whereby the use and cost of chemicals and power used for deposit removal can be kept to a minimum with a consequential low level of contamination of the seawater used for cooling.

I claim:

1. A method of monitoring the build-up of biological deposits on surfaces immersed in water, comprising the steps of:

continuously passing the water through a galvanic cell having a pair of dissimilar metal electrodes on at least one of which build-up of biological deposits is expected to occur;

monitoring galvanic current developed between the electrodes; and monitoring changes in the galvanic current to obtain an indication of the build-up of deposits on the electrodes.

2. Apparatus for monitoring the build-up of biological deposits on surfaces immersed in water, comprising:
a housing;
a pair of opposed plate members of dissimilar metals within said housing, defining a passage for the water to flow therebetween as the water flow through said housing forming electrodes; and
means for monitoring galvanic current developed between the plate electrodes to indicate the build-up of biological deposits on said plate electrodes.

3. Apparatus as claimed in claim 2, wherein the housing comprises a tubular member open at both ends and adapted for connection in a tube through which water flows.

4. Apparatus as claimed in claim 3, wherein the electrodes extend the length of the tubular member.

5. Apparatus as claimed in claim 2, wherein the electrodes have equal area facing surfaces.

6. Apparatus as claimed in claim 2, further comprising an insert member within said housing and mounting said electrodes and cooperating with said electrodes to define the passage.

7. Apparatus for monitoring the build-up of biological deposits on surfaces immersed in water, comprising:
a housing;
a pair of opposed electrodes of dissimilar metals within said housing, having equal-sized facing surfaces, and defining a passage for the water to flow therebetween as the water flows through said housing; and
means for monitoring galvanic current developed between the electrodes to indicate the build-up of biological deposits on said electrodes.

8. Apparatus as claimed in claim 7, wherein the housing comprises a tubular member open at both ends and adapted for connection in a tube through which water flows.

9. Apparatus as claimed in claim 8, wherein the electrodes extend the length of the tubular member.

10. Apparatus as claimed in claim 8, wherein the electrodes are formed as plate electrodes.

11. Apparatus as claimed in claim 7, further comprising an insert member within said housing and mounting said electrodes and cooperating with said electrodes to define the passage.

* * * * *